United States Patent
Tabet (12)

(10) Patent No.: US 6,859,279 B1
(45) Date of Patent: Feb. 22, 2005

(54) METHOD OF MEASURING SMALL PADS ON A SUBSTRATE

(75) Inventor: Milad F. Tabet, Santa Clara, CA (US)

(73) Assignee: Nanometrics Incorporated, Milpitas, CA (US)

( * ) Notice: Subject to any disclaimer, the term of this patent is extended or adjusted under 35 U.S.C. 154(b) by 360 days.

(21) Appl. No.: 10/058,263

(22) Filed: Jan. 25, 2002

(51) Int. Cl.[7] ................................................ G01J 4/00

(52) U.S. Cl. ...................................... 356/369; 356/364

(58) Field of Search ............................... 356/369, 364, 356/368, 237.1, 239.3

(56) References Cited

U.S. PATENT DOCUMENTS 5,596,406 A * 1/1997 Rosencwaig et al. ....... 356/327
6,707,056 B2 * 3/2004 Fanton et al. .......... 250/559.44

* cited by examiner

*Primary Examiner*—Frank G. Font
*Assistant Examiner*—Roy M. Punnoose
(74) *Attorney, Agent, or Firm*—Silicon Valley Patent Group LLP

(57) ABSTRACT

A method of measuring a small area on a substrate with an ellipsometer, comprising orienting a substrate with respect to the ellipsometer such that an elliptical light spot produced by the ellipsometer fits diagonally within the test area. Then measuring the surface properties of the substrate within the test area with the ellipsometer.

14 Claims, 5 Drawing Sheets

METHOD OF MEASURING SMALL PADS ON A SUBSTRATE

BACKGROUND

1. Field of the Invention

The present invention relates to a method of measuring surface properties within small areas on substrates, and more particularly a method of using an ellipsometer to measure within small pads on semiconductor wafers.

2. Description of Related Art

Spectroscopic ellipsometers are well-known metrology tools useful in a variety of scientific or technological fields, for example, biology, geology, forensics, nutrition science, medicine, and semiconductor processing, as well as manufacturing of flat panel displays and read/write and glide heads. Spectroscopic ellipsometers are instruments that measure the alteration of the polarization of light that is reflected from a sample. Ellipsometers typically reflect a known polarization state of polarized light at an oblique angle off the sample and detect any changes to the polarization state of the light. Changes in the polarization state of the light can be used to determine specific properties of the sample or films on the sample.

In one application, ellipsometers are used to accurately and precisely measure the properties of thin films on flat substrates, such as wafers or flat panel displays. Most commonly, ellipsometers are used as "stand-alone" metrology tools such as that disclosed in U.S. Pat. No. 5,596,406.

Spectroscopic ellipsometers gather more information, and thus provide better measurements, than single wavelength ellipsometers. However, spectroscopic ellipsometers have larger spot sizes, which limits their ability to measure within small areas. Moreover in the semiconductor industry, there continues to be a drive to miniaturize components of integrated circuits. In addition to other problems, miniaturization requires the measurement of surface characteristics within increasingly smaller areas. Thus, what is needed is a cost-effective method of measuring within small areas on substrates using an ellipsometer.

SUMMARY

In one embodiment of the present invention, a method of measuring a small area on a substrate with an ellipsometer comprises orienting a substrate with respect to the ellipsometer such that an elliptical light spot produced by the ellipsometer fits diagonally within the test area. Then measuring the surface properties of the substrate within the test area with the ellipsometer.

In accordance with a second embodiment of the present invention, a substrate is loaded onto a stage. The substrate is then oriented such that a spot produced by an ellipsometer fits diagonally within a test area to be measured. The ellipsometer then measures the surface properties of the substrate within the desired test area. In another embodiment of the present invention, a substrate is oriented prior to being loaded onto a stage.

DETAILED DESCRIPTION

Figure 1:
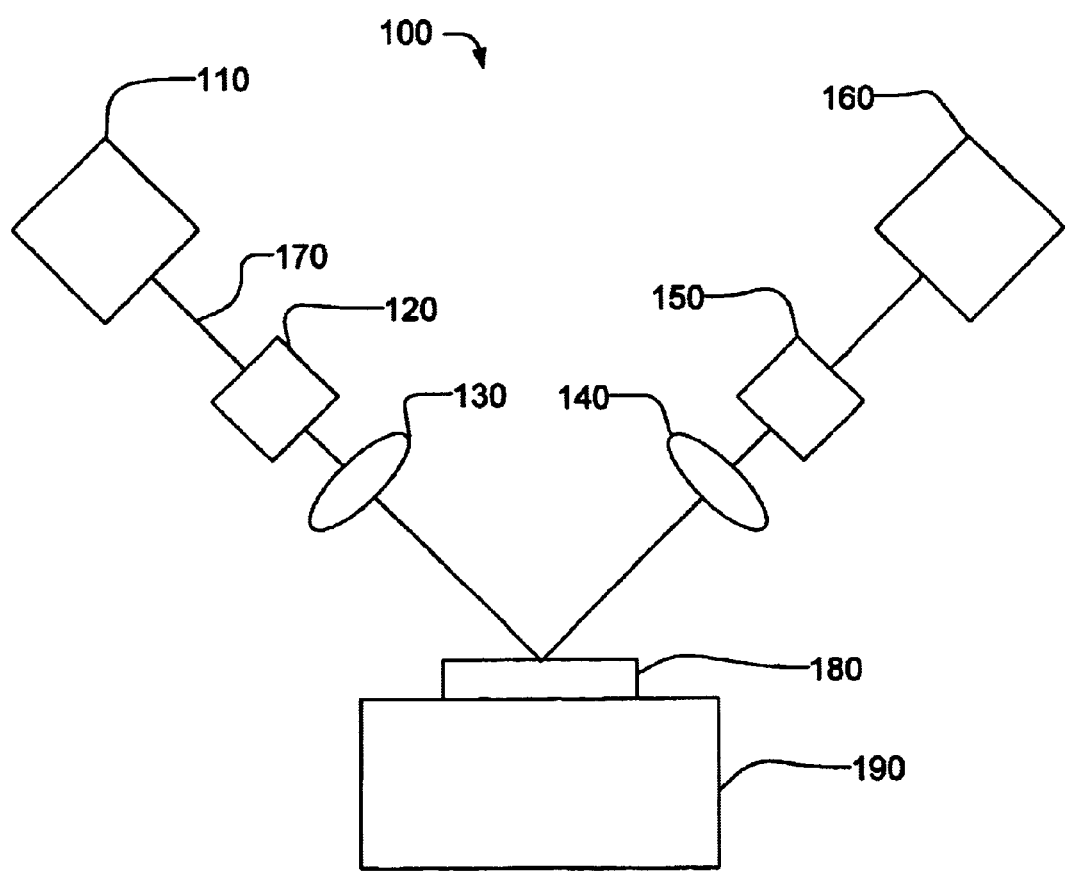
FIG. 1 shows an ellipsometer that may be used with the present invention.

FIG. 1 shows the optics of a conventional ellipsometer 100, which is used to make characteristic measurements of a substrate 180 mounted on a stage 190. The conventional ellipsometer 100 is often part of a metrology tool which may comprise other various systems (not shown) such as focusing and viewing optics, a reflectometer, or an interferometer.

The ellipsometer 100 includes a light source 110, a Polarization State Generator (PSG) 120, a number of optical lenses (shown as lenses 130 and 140), a Polarization State Detector (PSD) 150, and a light detector 160. A beam of light 170 is produced by light source 110 and is passed through PSG 120. The PSG 120 creates a known polarization state in light beam 170, which may vary with time. The polarized light beam 170 is reflected from the substrate 180 and the PSD 150 determines the polarization state of the light beam 170 after it has reflected from the substrate 180. The light detector 160 detects the intensity of the reflected light. The information provided by PSD 150 and light detector 160 may then be used to analyze surface characteristics of the substrate 180. Ellipsometric measurements are typically made with an angle between the light beam 170 and the reflecting substrate 180. Typically, the angle of incidence may vary from 20-degrees to 90-degrees, depending on the type of ellipsometer.

It should be understood that FIG. 1 is an exemplary ellipsometer. The present invention is not limited to use with the ellipsometer described in FIG. 1, but may be used with any ellipsometer. For example, ellipsometer 100 may be a single wavelength ellipsometer, with light source 110 being a single wavelength light source, e.g., a laser diode. Alternatively, light source 110 may produce light of several wavelengths and ellipsometer 100 may be a spectroscopic ellipsometer. Furthermore, ellipsometer 100 may use a CCD array, a photodiode array, or a photomultiplier array as detector 160 and may use rotating elements.

Figure 2:
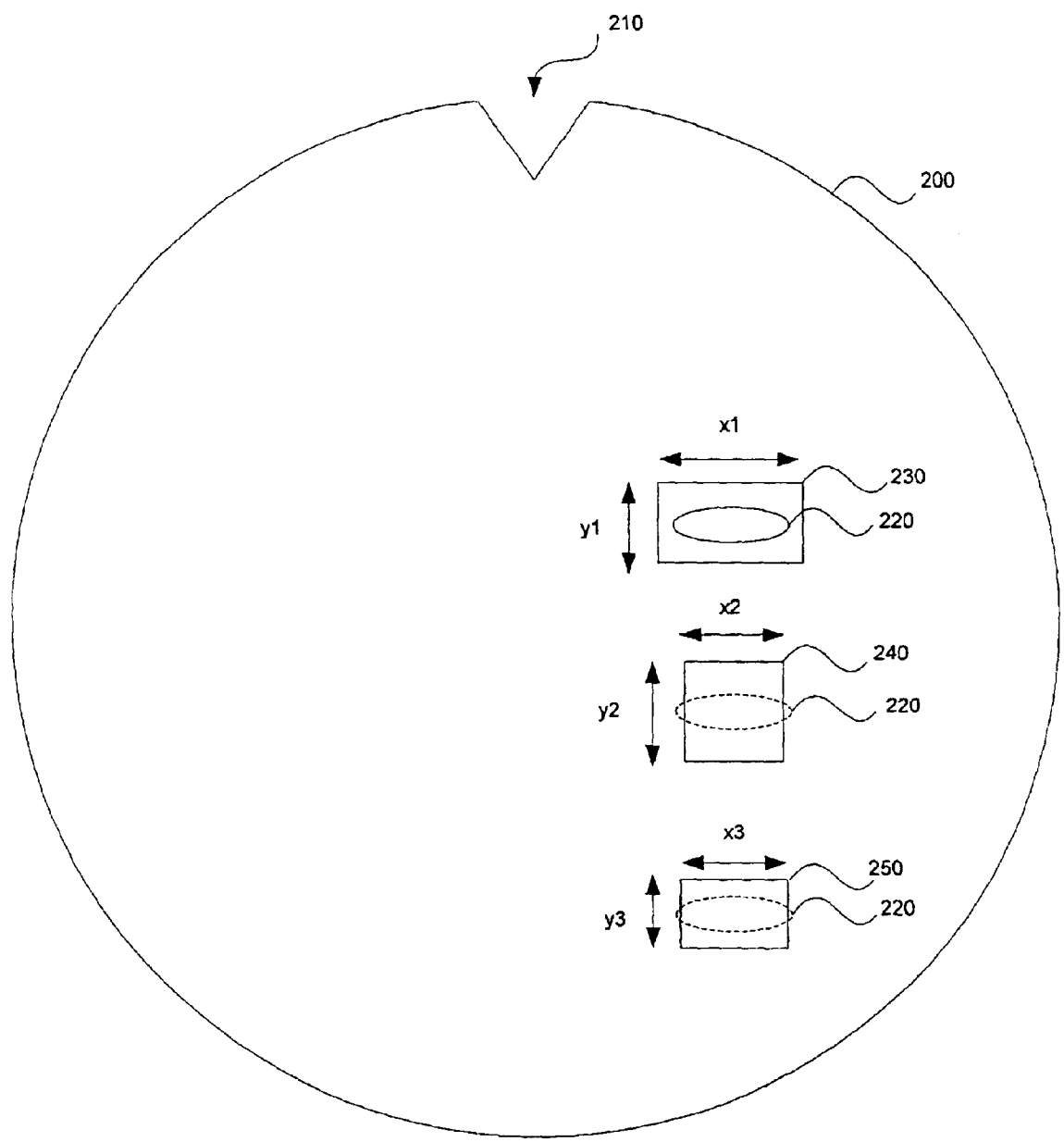
FIG. 2, FIG. 3, and FIG. 4 are top views of a substrate showing pads and ellipsometer spots.

In manufacturing of integrated circuits (ICs) ellipsometric measurements of test sites referred to herein as "pads" are common. Pads are areas on a substrate typically, but not necessarily, located in the scribe lines. Pads are tested to determine how processing of the entire substrate is proceeding. The testing of pads after various stages of processing ensures that the processing of a substrate is proceeding as desired. Three exemplary pads of varying sizes are shown in FIG. 2 as pads 230, 240, and 250. It should be understood that FIG. 2 is not to scale and serves illustrative purposes only.

To measure pads on substrate 200, substrate 200 is placed on a stage, e.g., stage 190 (FIG. 1), which moves substrate 200 so that any area on the surface of the substrate 200 can be measured. Substrate 200 has a notch 210 on its perimeter. Notch 210 is used to accurately determine the orientation of substrate 200. Notch 210 is used with an alignment system to align substrate 200 prior to loading onto the stage or prior to taking measurements from the surface of substrate 200. Conventionally, the substrate 200 is oriented at 0-degrees or 90-degrees when measuring pads on the substrate surface. FIG. 2 shows substrate 200 at a conventional 90-degree orientation.

Also shown in FIG. 2 is a light spot 220. Spot 220 is the area on substrate 200 where a light beam from an ellipsometer, e.g., light beam 170 is incident and reflected. The area of spot 220 on substrate 200 is the measurement area where ellipsometer measurements are taken. Thus, in order to measure the properties within a specific area on substrate 200, spot 220 must fit within the desired area to be measured. Typical ellipsometers produce an elliptical shaped spot due to light beam 170 having an angle of incidence. For example, a conventional ellipsometer produces an elliptical spot with a major axis of 70 μm and a minor axis of 35 μm.

Shown in FIG. 2 is a conventional pad 230, defined by dimensions x1 and y1. In conventional pads, x1 is typically 80 micrometers and y1 is typically 60 micrometers. Thus, a spot 220 of dimensions 70 μm×35 μm can easily fit within a conventional pad 230 as is shown in FIG. 2. As stated above, substrate 200 is in the conventional 90-degree orientation. Therefore, the surface properties of pad 230 can be ellipsometrically measured using a conventional ellipsometer and conventional measuring procedure.

However, the current trend in the semiconductor processing industry is to reduce pad sizes. For example, pad 240 shown in FIG. 2 has dimensions of 55 micrometers (x2) by 55 micrometers (y2). Spot 220 is shown in dotted lines overlying pad 240 for the sake of comparison. Pad 240 is representative of the trend towards smaller pad sizes. The conventional technique of orienting substrate 200 at 0-degrees or 90-degrees does not allow ellipsometric measurements to be made within pad 240, as shown in FIG. 2. Similarly, pad 250 with dimensions of 65 micrometers (x3) by 50 micrometers (y3) cannot be measured using the conventional technique of orientating substrate 200 at 0-degrees or 90-degrees. Again, spot 220 is shown in dotted lines overlying pad 250 for purposes of comparison. The size of spot 220 is difficult to reduce because it is dependent on a number of optical components in the ellipsometer, and the wavelength of the light beam. Thus, a need exists for a technique, which allows ellipsometric measurements to be made within small pad sizes such as pads 240 and 250, without costly and difficult reengineering of the ellipsometer.

Figure 3:
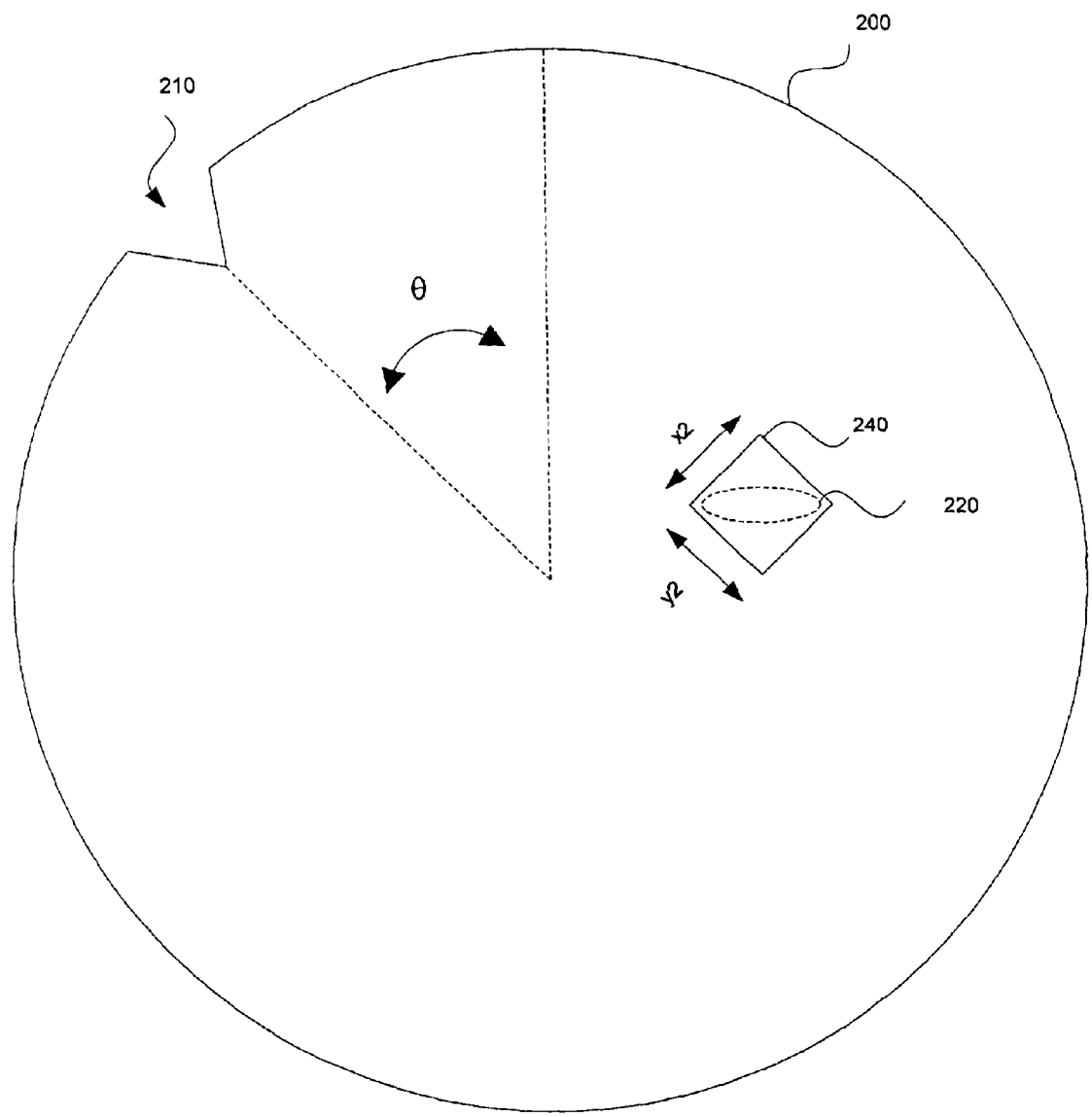

In accordance with one embodiment of the present invention, FIG. 3 shows substrate 200 oriented at an angle θ with respect to normal. The appropriate angle θ of substrate orientation depends on the dimensions of the pad being measured. In the case of a square pad such as pad 240, the appropriate angle θ is 45 degrees. As can be seen in FIG. 3, when substrate 200 is oriented at 45 degrees spot 220 fits within pad 240 along the diagonal of pad 240, i.e., the major axis of spot 220 is approximately aligned with the diagonal of pad 240. Orienting substrate 200 with respect to spot 220 such that spot 220 fits diagonally within pad 240, solves the problem with conventional substrate orientations, and allows ellipsometric measurements to be made within pad 240. It should be understood that the orientation of substrate 200 is with respect to spot 220, thus the orientation of substrate 200 may be changed by rotating substrate 200 or by rotating the ellipsometer producing spot 220.

Figure 4:
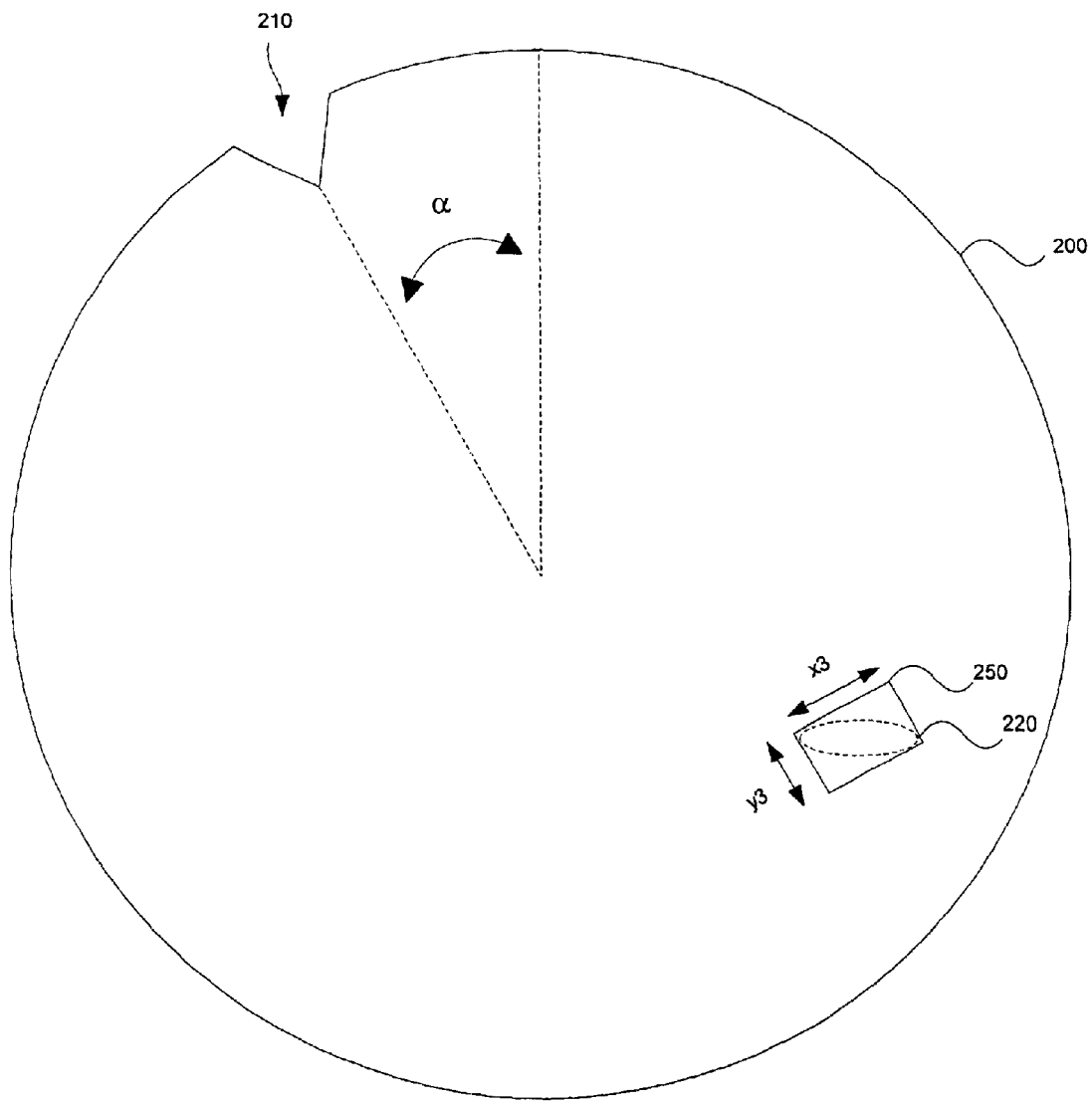

The disclosed method of orienting substrate 200 so that the major axis of spot 220 fits diagonally within pad 240 may be utilized when measuring areas that are not square. In accordance with a second embodiment of the present invention, FIG. 4 shows substrate 200 oriented at an angle α with respect to the standard 90-degree orientation. The angle α is based on the angle of the diagonal in the rectangular pad 250. Thus, as can be seen in FIG. 4, the major axis of spot 220 is approximately aligned with the diagonal of pad 250. When x3 is 60 μm and y3 is 50 μm, orienting substrate 200 at a 37.6-degree angle advantageously allows ellipsometric measurements to be made within pad 250.

Thus, it should be understood that the present invention includes determining the angle of diagonal of a pad and orienting a substrate to that angle in order to fit an ellipsometric spot diagonally within the pad. The angle of diagonal for a rectangular area may be calculated using the following equation:

Angle of Diagonal=arctangent (short rectangular side/long rectangular side)

A substrate may then be oriented at the calculated angle of diagonal. Thus, a range of substrate orientations is within the scope of the present invention.

Moreover, it should be understood that the major axis of spot 220 need only be approximately aligned with the diagonal of a pad. For example, the angle of the major axis of spot 220 may be offset by a small amount from the diagonal of the pad, as long as the spot fits diagonally within the pad.

Figure 5:
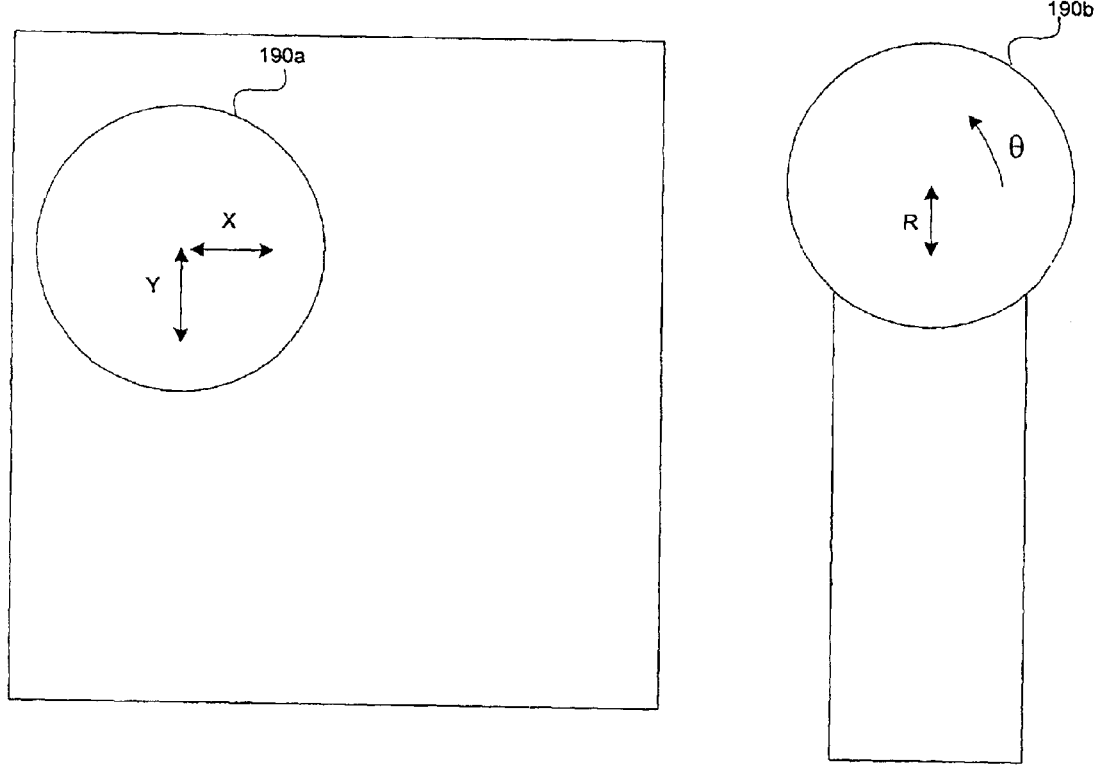
FIG. 5 is a top view of two stages that may be used with the present invention.

FIG. 5 shows a top view of two stages that may be used with the present invention. Shown in FIG. 5 is stage 190*a*, which is an X-Y stage. Stage 190*a* is only capable of movement in two independent orthogonal directions X and Y. In accordance with one embodiment of the present invention an X-Y stage is used to ellipsometrically measure a test area on a substrate, e.g., substrate 200. An ellipsometer producing a spot, e.g., spot 220 is then rotated so that substrate 200 has the desired orientation with respect to spot 220, namely an orientation that allows spot 220 to fit diagonally within the test area. However, ellipsometers comprise precisely aligned optics that could shift when being rotated. Therefore, in an alternative embodiment, software controlling the loading of substrate 200 onto stage 190*a* may be programmed to load substrate 200 at a desired orientation, e.g., at a 45-degree angle. Methods of loading substrates onto stages are well known in the art.

Also shown in FIG. 5 is an R-θ stage 190*b*. Stage 190*b* is capable of linear movement shown as R-motion in FIG. 5. Additionally, stage 190*b* is capable of rotation shown in FIG. 5 as θ-motion. In accordance with another embodiment of the present invention, substrate 200 may first be loaded onto stage 190*b* at any orientation. Software controlling the θ-motion of stage 190*b* may then rotate substrate 200 to the desired orientation. Of course, any desired R-θ stage may be used, such as that disclosed in U.S. Pat. No. 6,320,609. It should be understood that any method by which a substrate is oriented so that an ellipsometer spot fits diagonally within an area to be measured, may be used with the present invention.

Although the present invention has been described in detail with reference to certain versions thereof, other versions are possible. For example, while the test areas that are measured in accordance with the present invention are described as pads on a semiconductor wafer, it should be understood, that the test area may be any desired area on a substrate, including flat panel displays and read/write and glide heads. Therefore, the spirit and scope of the appended claims should not be limited to the description of the versions depicted in the figures.

What is claimed is:

1. A method of ellipsometrically measuring a test area on a substrate, the method comprising:

orienting said substrate with respect to an ellipsometer so that an elliptical light spot produced by said ellipsometer fits diagonally within said test area; and measuring the surface properties of said test area with said ellipsometer.

2. The method of claim 1, further comprising determining an angle of diagonal of said test area.

3. The method of claim 2, wherein said orienting comprises rotating said substrate by a predetermined angle, so that a major axis of said elliptical light spot is approximately aligned with said angle of diagonal of said test area.

4. The method of claim 2, wherein said orienting comprises rotating said ellipsometer by a predetermined angle, so that a major axis of said elliptical light spot is approximately aligned with said angle of diagonal of said test area.

5. A method of measuring a test area on a substrate using an elliptical light spot produced by an ellipsometer, the method comprising:

loading a substrate onto a stage;

orienting said substrate with respect to said ellipsometer so that said elliptical light spot fits diagonally within said test area;

producing a light beam with an ellipsometer, said light beam creating said elliptical light spot on said substrate when reflected off of said substrate; and measuring the surface properties of said test area with said ellipsometer.

6. The method of claim 5, wherein said elliptical light spot comprises a major axis and a minor axis, said major axis of said elliptical light spot being approximately aligned with a diagonal of said test area.

7. The method of claim 5, wherein said sample is loaded onto said stage with the desired orientation.

8. The method of claim 5, wherein said orienting comprises rotating said substrate by a predetermined angle.

9. The method of claim 5, wherein said orienting comprises rotating said ellipsometer by a predetermined angle.

10. The method of claim 5, further comprising calculating an angle of diagonal for said test area, and orienting said substrate with respect to said ellipsometer by said angle of diagonal.

11. A method of measuring a test area on a substrate using an elliptical light spot produced by an ellipsometer, wherein said elliptical light spot has a major axis and a minor axis, the method comprising:

loading a substrate onto a stage;

orienting said substrate with respect to said ellipsometer, so that said major axis of said elliptical light spot is approximately aligned with a diagonal of said test area;

producing a light beam with an ellipsometer, said light beam creating said elliptical light spot on said substrate when reflected off of said substrate; and measuring the surface properties of said test area with said ellipsometer.

12. The method of claim 11, wherein said orienting comprises rotating said substrate by a predetermined angle.

13. The method of claim 11, wherein said orienting comprises rotating said ellipsometer by a predetermined angle.

14. The method of claim 11, further comprising calculating an angle of said diagonal, and orienting said substrate with respect to said ellipsometer by said angle of said diagonal.

* * * * *